US006200956B1

(12) United States Patent
Scherman et al.

(10) Patent No.: US 6,200,956 B1
(45) Date of Patent: *Mar. 13, 2001

(54) NUCLEIC ACID-CONTAINING COMPOSITION, PREPARATION AND USE THEREOF

(75) Inventors: Daniel Scherman, Paris; Gérardo Byk, Creteil; Bertrand Schwartz, Maisons Alford, all of (FR)

(73) Assignee: Aventis Pharma S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/306,044

(22) Filed: May 6, 1999

Related U.S. Application Data

(63) Continuation of application No. 08/894,339, filed as application No. PCT/FR96/00248 on Feb. 15, 1996, now Pat. No. 5,945,400.

(30) Foreign Application Priority Data

Feb. 17, 1995 (FR) .................................................. 95 01865

(51) Int. Cl.[7] .......................... A61K 38/00; A61K 38/04; C07K 14/00; C07K 16/00

(52) U.S. Cl. .................................. 514/13; 514/12; 514/14; 514/15; 530/300; 530/326; 530/327; 530/328

(58) Field of Search ............................... 424/450; 514/44, 514/12, 13, 14; 435/458; 536/23.1, 24.5; 530/300, 326, 327, 328

(56) References Cited

U.S. PATENT DOCUMENTS

| | | | |
|---|---|---|---|
| 5,354,844 | 10/1994 | Beug et al. | 530/345 |
| 5,476,962 | 12/1995 | Behr et al. | 560/168 |

FOREIGN PATENT DOCUMENTS

| | | |
|---|---|---|
| 0 140 308 A2 | 5/1985 | (EP) . |
| 0 185 573 A1 | 6/1986 | (EP) . |
| 0 259 212 A1 | 3/1988 | (EP) . |
| 0 321 201 A2 | 6/1989 | (EP) . |
| 0 388 758 | 9/1990 | (EP) . |
| 0 424 688 A2 | 5/1991 | (EP) . |
| 2 646 161 | 10/1990 | (FR) . |
| WO 90/11092 | 10/1990 | (WO) . |
| WO 91/17773 | 11/1991 | (WO) . |
| WO 93/06223 | 4/1993 | (WO) . |
| WO 93/19191 | 9/1993 | (WO) . |
| WO 93/19768 | 10/1993 | (WO) . |
| WO 94/05624 | 3/1994 | (WO) . |
| WO 94/24297 | 10/1994 | (WO) . |
| WO 94/25608 | 11/1994 | (WO) . |
| WO 94/25073 | 11/1994 | (WO) . |
| WO 95/30330 | 11/1995 | (WO) . |
| WO 96/02655 A1 | 2/1996 | (WO) . |
| WO 96/17823 | 6/1996 | (WO) . |
| WO 96/25508 | 8/1996 | (WO) . |

OTHER PUBLICATIONS

Singhal et al, in "Gene Therapeutics", Ed. Wolff, Jon A., Birkhauser Boston, pp. 118–142 Mar. 1994.*
Emery et al., Stern Cell Gene Therapy . . . , Annals New York Acad. Sci., pp. 94–108 Apr. 1999.*
Anderson, W.F., Human Gene Therapy, Nature 392, suppl., pp. 25–30, Apr. 1998.*
Kuehl et al., Relationship between the Structure of Chromosomal Protein HMG1 and Its Accumulation in the Cell Nucleus, J. Biol. Chem., vol. 260, No. 18, pp. 10361–10368 (1985).
Wienhues et al., A Novel Method for Transfection and Expression of Reconstituted DNA–Protein Complexes in Eukaryotic Cells, DNA, vol. 6, No. 1, pp. 81–89 (Feb. 1, 1987).
Bottger et al., Condensation of vector DNA by the chromosomal protein HMG1 results in efficient transfection, Biochimica et Biophysica Acta, vol. 950, No. 2, pp. 221–228 (Jul. 13, 1988).
Bianchi et al., Specific Recognition of Cruciform DNA by Nuclear Protein HMG1, Science, vol. 243, pp. 1056–1059 (Feb. 24, 1989).
Cornetta et al., Protamine sulfate as an effective alternative to polybrene in retroviral–mediated gene–transfer: implications for human gene therpy, J.Virol.Methods, vol. 23, No. 2, pp. 187–194 (Feb. 1, 1989).
Bottger et al., Transfection by DNA–nuclear protein HMG1 complexes: Raising efficiency and role of DNA topology, Arch. Geschwulstforsch., vol. 60, No. 4, pp. 265–270 (1990).
Bustin et al., Structural features of the HMG chromosomal proteins and their genes, Biochimica et Biophysica Acta, vol. 1049, pp. 231–243 (1990).
Bianchi, Production of functional rat HMG1 protein in Escherichia coli, Gene, vol. 104, pp. 271–275 (1991).
Kato et al., Expression of Hepatitis B Virus Surface Antigen in Adult Rat Liver, J.Biol.Chem., vol. 266, No. 6, pp. 3361–3364 (Feb. 25, 1991).
Griess et al., Phylogenetic Relationships of HMG Box DNA–Binding Domains, J. Mol. Evol., vol. 37, pp. 204–210 (1993).
Maxwell et al., Binding of cellular proteins to a conformational domain of tumor supressor protein p.53, Oncogene, vol. 8, pp. 3421–3429 (1993).

(List continued on next page.)

Primary Examiner—Robert A. Schwartzman
Assistant Examiner—Karen Lacourciere
(74) Attorney, Agent, or Firm—Aventis Pharmaceuticals Products Inc.

(57) ABSTRACT

Pharmaceutical composition useful for transfecting a nucleic acid and characterised in that it contains, in addition to the nucleic acid, at least one transfecting agent and a compound causing the condensation of the nucleic acid, wherein the compound is totally or partly derived from a histone, a nucleoline, a protamine and/or a derivative thereof. The use of the composition for transferring nucleic acids in vitro, ex vivo and/or in vivo is also described.

36 Claims, No Drawings

OTHER PUBLICATIONS

Isakov et al., Loss of Expression of Transplantation Antigens Encoded by the H–2K Locus on Lewis Lung Carcinoma Cells and Its Relevance to the Tumor's Metastatic Properties, JNCI, vol. 71, No. 1, pp. 139–145 (Jul. 1983).

Hofmann et al., Hepatocyte–Specific Gene Delivery and Expression Using a HBV–Derived Composite Vector System, Gene Ther. Meet. Cold Spring Harbor, p. 193 (1994).

Morishita et al., Novel Strategies to Enhance the Efficacy of Antisense Oligonucleotides for In Vivo Gene Therapy, J.Cell.Biochem., Suppl. No. 18A, p. 239 (1994).

Stros et al., DNA looping by the HMG–box domains of HMG1 and modulation of DNA binding by the acidic C–terminal domain, Nucleic Acid Research, vol. 22, No. 6, pp. 1044–1051 (1994).

Kohlstaedt et al., Effect of pH on Interactions between DNA and High–Mobility Group Protein HMG1, Biochemistry, vol. 33, pp. 12702–12707 (1994).

Davis, The Nuclear Pore Complex, Annu. Rev. Biochem. vol. 64, pp. 865–96 (1995).

Sandig et al., Direct gene transfer of HMG1 based DNA–protein complexes, J.Mol.Med., vol. 73, No. 4, p. B10 (Apr. 24, 1995).

Strauss et al., Novel vectors to liver–directed gene transfer, J.Mol.Med., vol. 73, No. 4, p. B12 (Apr. 24, 1995).

Kaneda et al., Increased expression of DNA cointroduced with nuclear protein in adult rat liver, J.Mol.Med., vol.73, No. 6, pp. 289–279 (Jun. 1995).

Wako invents gene transfection reagent, Biotech. Newswatch, p. 12 (Aug. 7, 1995).

Orkin et al., Report and Recommendations of the Panel to Assess the NIH Investment in Research on Gene Therapy, (Dec. 7, 1995).

* cited by examiner

NUCLEIC ACID-CONTAINING COMPOSITION, PREPARATION AND USE THEREOF

This application is a continuation of U.S. application Ser. No. 08/894,339, filed Aug. 15,1997, now U.S. Pat. No. 5,945,400 which was the National Stage of International Application No. PCT/FR96/00248, filed Feb. 15,1996.

The present invention concerns the field of gene therapy and relates more particularly to the in vitro, ex vivo and/or in vivo transfer of genetic material. The invention proposes in particular a novel pharmaceutical composition which is useful for efficiently transfecting cells. The invention also relates to the uses of this composition.

Chromosomal deficiencies and/or anomalies (mutation, aberrant expression, and the like) are the cause of many diseases, of hereditary or non-hereditary nature. Conventional medicine has for a long time remained powerless as far as they are concerned. Nowadays, with the development of gene therapy, it is hoped to be able from now on to prevent or correct this type of chromosomal aberration. This novel medication consists in introducing genetic information into the affected cell or organ, for the purpose of correcting this deficiency or anomaly therein or alternatively for the purpose of expressing a protein of therapeutic value therein.

The main obstacle to the penetration of a nucleic acid into a cell or target organ lies in its size and the polyanionic nature of this nucleic acid, which oppose its passage across cell membranes.

In order to relieve this difficulty, various techniques are nowadays proposed including, more particularly, the transfection of naked DNA across the plasma membrane in vivo (WO90/11092) and the transfection of DNA via a transfection vector.

As regards the transfection of naked DNA, the efficacy of this still remains very low. Naked nucleic acids possess a short half-life in plasma on account of their degradation by enzymes and their removal via urinary routes.

Regarding the second technique, this also proposes two strategies:

The first uses natural transfection vectors, namely viruses. It is thus proposed to use adenoviruses, herpesviruses, retroviruses and, more recently, adeno-associated viruses. Although these vectors prove to be of high performance as regards transfection, it is unfortunately not possible to exclude as far as they are concerned certain risks of pathogenicity, replication and/or immunogenicity, which are inherent to their viral nature.

The second strategy consists advantageously in using non-viral agents capable of promoting the transfer and expression of DNA in eukaryotic cells.

The subject of the present invention is directed more particularly towards this second strategy.

Chemical or biochemical vectors represent an advantageous alternative to natural viruses, in particular for this absence of viral recombination and/or immunological response. They have no pathogenic power, there is no risk of multiplication of the DNA within these vectors and there is no theoretical limit associated therewith as regards the size of the DNA to be transfected.

These synthetic vectors have two main functions, to condense the DNA to be transfected and to promote its cell binding as well as its passage across the plasma membrane and, where appropriate, the two nuclear membranes.

On account of its polyanionic nature, DNA naturally has no affinity for the plasma membrane of cells, which membrane is also polyanionic. In order to overcome this drawback, non-viral vectors generally all have polycationic charges.

Among the synthetic vectors developed, cationic polymers of polylysine and DE dextran type or alternatively cationic lipids or lipofectants are the most advantageous. They have the property of condensing DNA and of promoting its association with the cell membrane. More recently, the concept of targeted transfection mediated by a receptor has been developed. This technique exploits the principle of condensing DNA, by virtue of the cationic polymer, while at the same time directing the binding of the complex to the membrane using a chemical coupling between the cationic polymer and the ligand of a membrane receptor present at the surface of the cell type which it is desired to graft. Screenings of the receptor with transferrin and insulin, and screening of the hepatocyte asialoglycoprotein receptor have thus been described.

However, the synthetic vectors proposed to date are still far from giving as good performance as viral vectors. This could be the consequence of insufficient condensation of the DNA to be transfected and/or difficulties, encountered by the transfected DNA, of leaving the endosome and penetrating into the cell nucleus. Lastly, other drawbacks are directly associated with the nature of the cationic polymers of the lipofectants used.

The subject of the present invention is precisely to propose an advantageous solution to these problems.

More precisely, the present invention relates to a pharmaceutical composition which is useful for the transfection of a nucleic acid, characterized in that it contains, besides the said nucleic acid, at least one transfection agent and a compound involved in the condensation of the said nucleic acid; the said compound being derived, partly or totally, from a histone, a nucleoline, a protamine and/or one of the derivatives thereof.

The Applicant has discovered, unexpectedly, that the presence of such a compound within a transfecting composition based on a standard transfection agent made it possible to reduce considerably the amount of this agent, with the beneficial toxicological consequences stemming therefrom, without bringing any prejudice to bear on the transfecting activity of the said composition. On the contrary, this composition advantageously has a higher level of transfection.

In the sense of the invention, a compound involved in the condensation of the nucleic acid covers any compound which directly or indirectly compacts the nucleic acid. More precisely, this compound may either act directly on the nucleic acid to be transfected or may be involved at the level of an associated compound which itself is directly involved in the condensation of this nucleic acid.

Preferably, it acts directly on the nucleic acid.

According to a specific embodiment of the invention, the compound involved in the condensation of the nucleic acids consists, totally or partly, of peptide units (LysThrProLysLysAlaLysLysPro) SEQ ID No. 1 and/or (AlaThrProAlaLysLysAlaAla) SEQ ID No. 2 or one of their derivatives, it being possible for the number of units to range between 2 and 10. In the structure of the compound according to the invention, these units may be repeated continuously or non-continuously. Thus, they may be separated by connections of biochemical nature, for example one or more amino acids, or of chemical nature.

The particular choice, a compound according to the invention, of a peptide or pseudopeptide possessing a majority of amino acids with basic nature, such as lysine, histidine or arginine, is particularly advantageous in the context of the present invention. This compound may also possess a β-sheet conformational structure. Basic amino acids are, indeed, more specifically involved in peptide-nucleic acid bonding. They participate in the establishment of ionic hydrogen bonds between the two species, thus promoting the condensation of the nucleic acid. As regards the 8-sheet structure, this is characterized by better accessibility of the majority of the carbonyl bonds and of the hydrogen atoms which, on account of their respective acceptor and donor natures, also favour the formation of bonds with the nucleic acid to be compacted.

Such a compound is more preferably all or part of a histone, a nucleoline, protamine and/or one of the derivatives thereof.

Histones and protamines are cationic proteins which naturally compact DNA. They are thus responsible in vivo for the condensation of non-transcribed DNA and the DNA of certain viruses. As histones which may be used in the context of the present invention, mention may be made more particularly of histones H1, H2a, H3 and H4. As regards nucleoline, this is a nucleolar protein which would appear to possess a synergistic effect with respect to the histone H1 during the condensation of DNA by the latter. In the context of the present invention, the compound may advantageously be represented by a peptide sequence derived from the N-terminal part of nucleoline, and more precisely corresponding to the sequence (AlaThrProAla-LysLysAlaAlaAlaThrProAlaLysLysAlaAla) (COOH)(SEQ ID No. 3).

Preferably, the compound used according to the invention is a sequence derived from histone H1 and more preferably from its C-terminal domain and more particularly corresponds to the sequence (LysThrProLysLysAlaLys-LysProLysThrProLysLysAlaLysLysPro) (COOH) (SEQ ID No. 4).

As an illustration of this family of compounds according to the invention, mention may also be made of the following oligopeptides:
AlaThrProLysLysSerAlaLysLysThrProLysLysAlaLysLys-Pro (COOH). (SSEQ ID No. 5) and
LysLysAlaLysSerProLysLysAlaLysAlaAlaLysPro-LysLysAlaProLysSerProAlaLysAlaLysAla (COOH). (SEQ ID No. 6).

As regards more particularly the sequences derived from protamines which can also be used in the context of the present invention, the following oligopeptides may be proposed in particular:
SerArgSerArgTyrTyrArgGlnArgGlnArgSerArgArgArg-ArgArgArg (COOH). (SEQ ID No.7) and
ArgArgArgLeuHisArgIleHisArgArgGlnHisArgSerCysArg-ArgArgLysArgArg (COOH). (SEQ ID No. 8)

In the sense of the present invention, the term derivative denotes any peptide, pseudopeptide (peptide incorporating non-biochemical elements) or protein differing from the protein or peptide considered, obtained by one or more genetic and/or chemical modifications. The expression genetic and/or chemical modification may be understood to mean any mutation, substitution, deletion, addition and/or modification of one or more residues of the protein considered. More precisely, the term chemical modification refers to any modification of the peptide or protein generated by chemical reaction or by chemical grafting of biological or non-biological molecule(s) onto any number of residues of the protein. The expression genetic modification is understood to refer to any peptide sequence the DNA of which hybridizes with these sequences or fragments thereof and the product of which possesses the activity indicated. Such derivatives may be generated for different purposes, such as in particular that of increasing the affinity of the corresponding polypeptide or its (their) ligand(s), that of improving its levels of production, that of increasing its resistance to proteases, that of increasing and/or modifying its activity, or that of imparting novel pharmacokinetic and/or biological properties thereto. Among the derivatives resulting from an addition, mention may be made, for example, of chimeric peptide sequences containing a supplementary heterologous part attached to one end. The term derivative also comprises protein sequences which are homologous with the sequence considered, derived from other cell sources and in particular from cells of human origin, or from other organisms, and possessing an activity of the same type. Such homologous sequences may be obtained by hybridization experiments on the corresponding DNA. The hybridizations may be performed with nucleic acid banks, using the native sequence or a fragment thereof as probe, under conditions of conventional stringency (Maniatis et al.), (cf. General techniques of molecular biology), or, preferably, under conditions of high stringency.

In one particularly advantageous embodiment, the compositions of the present invention also comprise a targeting element which makes it possible to direct the transfer of the nucleic acid. This targeting element may be an extracellular targeting element, which allows the nucleic acid transfer to be directed towards certain types of cells or certain desired tissues (tumour cells, liver cells, haematopoietic cells, and the like). Such an element may also be an intracellular targeting element, allowing the nucleic acid transfer to be directed towards certain favoured cell compartments (mitochondria, nucleus, and the like).

The targeting element is more preferably linked, covalently or non-covalently, to the compound according to the invention. The targeting element may also be linked to the nucleic acid. According to a preferred mode of the invention, the said compound is associated, via an additional heterologous part bound to one of its ends. Such parts may be, in particular, peptides of fusogenic type for promoting cellular transfection, that is to say for favouring the passage of the transfecting composition or its various elements across membranes, for helping in the egress from endosomes or for crossing the nuclear membrane. It may also be a cell receptor ligand present at the surface of the cell type, such as, for example, a sugar, transferrin, insulin or asialo-orosomucoid protein. Such a ligand may also be one of intracellular type, such as a nuclear location signal (nls) sequence which promotes the accumulation of transfected DNA within the nucleus.

Among the targeting elements which may be used within the context of the invention, mention may be made of sugars, peptides, hormones, vitamins, cytokines, oligonucleotides, lipids or sequences or fractions derived from these elements and which allow specific binding with the corresponding receptors. They are preferably sugars and/or peptides such as antibodies or antibody fragments, cell receptor ligands or fragments thereof, receptors or receptor fragments, and the like. In particular, they may be ligands of growth factor receptors, of cytokine receptors, of cell lectin receptors or of adhesion protein receptors. Mention may also be made of the receptor for transferrin, for HDLs and for LDLs. The targeting element may also be a sugar which makes it possible to target lectins such as the asialoglycoprotein receptors, or alternatively an antibody Fab fragment which makes it possible to target the Fc fragment receptor of immunoglobulins.

As an illustration of this type of association, use may be made in particular, in the context of the present invention, of a compound of type $H_1$-nls and more preferably a peptide possessing the sequence ProLysLysLysArgLysVal-βAla LysThrProLysLysAlaLysLysProLysThrProLysLysAla- LysLysPro (COOH) (SEQ ID No.9).

Advantageously, the compound according to the invention and more particularly any histone derivative, protamine derivative or nucleoline derivative may also be polyglycosylated, sulphonated and/or phosphorylated and/or grafted to complex sugars or to a lipophilic compound such as, for example, a polycarbon chain or a cholesterol derivative.

The composition according to the invention may obviously comprise several nucleic acid-compacting compounds, of different nature. It is thus possible to combine a compound of histone type with a compound of nucleoline type.

The compound according to the invention is present in a sufficient amount to compact the nucleic acid according to the invention. Thus, the compound/nucleic acid ratio (expressed in weight) may be between 0.1 and 10 and more preferably between 0.3 and 3.

As regards the transfection agent present in the composition according to the invention, it is preferably chosen from cationic polymers and lipofectants.

According to the present invention, the cationic polymer is preferably a compound of general formula I,

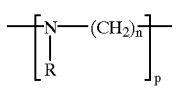

(I)

in which
R may be a hydrogen atom or a group of formula

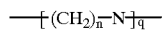

n is an integer between 2 and 10;
p and q are integers,
it being understood that the sum p+q is such that the average molecular weight of the polymer is between 100 and $10^7$ Da.

It is understood that, in the formula (I), the value of n may vary for the different units p. Thus, the formula (I) combines both homopolymers and heteropolymers.

More preferably, in the formula (I), n is between 2 and 5. In particular, the polyethyleneimine (PEI) polymers and polypropylene4mine (PPI) polymers exhibit entirely advantageous properties. The polymers preferred for carrying out the present invention are those whose molecular weight is between $10^3$ and $5 \cdot 10^6$. By way of example, mention may be made of polyethyleneimine of average molecular weight 50,000 Da (PEI50K) or polyethyleneimine of average molecular weight 800,000 Da (PEI800K).

PRI50K and PEI800K are commercially available. As regards the other polymers represented by the general formula I, they may be prepared according to the process described in patent application FR 94/08735.

In order to obtain an optimum effect for the compositions of the invention, the respective proportions of the polymer and the nucleic acid are preferably determined such that the molar ratio R=amines in the polymer/phosphates in the nucleic acid is between 0.5 and 50, more preferably between 5 and 30. Results which are most particularly advantageous are obtained using from 5 to 25 equivalents of polymer amines per charge of nucleic acid.

As regards more particularly the lipofectants, for the purposes of the invention, any compound with a lipid nature and which has already been proposed as an active agent with regard to the cellular transfection of nucleic acids is understood to be covered by this name. In general, these are amphiphilic molecules comprising at least one lipophilic region which may or may not be associated with a hydrophilic region. Representatives of the first family of compounds which may be proposed in particular are lipids capable of forming liposomes, such as POPCB, phosphatidylserine, phosphatidylcholine, cholesterol, maleimidophenylbutyrylphosphatidylethanolamine, lactosylceramide in the presence or absence of polyethylene glycol to form furtive liposomes, or, with or without antibodies or ligands, to form immunoliposomes or target liposomes.

According to a particular mode of the invention, the lipid agent used possesses a cationic region. This cationically charged cationic region, preferably polyamine, is capable of combining reversibly with the negatively charged nucleic acid. This interaction strongly compacts the nucleic acid. The lipophilic region renders this ionic interaction inaccessible to the external aqueous medium, by coating the. nucleolipid particle formed with a lipid film.

Thus, it is known that a positively charged cationic lipid, N-[1-(2,3-dioleyloxy)propyl]-N,N,N-trimethylammonium chloride (DOTMA), interferes, in the form of liposomes or small vesicules, spontaneously with DNA, which is negatively charged, to form lipid-DNA complexes capable of fusing with cell membranes, and thereby allows the DNA to be delivered into the cell. Since DOTMA, other cationic lipids have been proposed along this structural model: lipophilic group associated with an amino group via a so-called "spacer" arm. Among these, mention may be made more particularly of those comprising, as lipophilic group, two fatty acids or a cholesterol derivative, and also containing, where appropriate, as amino group, a quaternary ammonium group. DOTAP, DOBT and ChOTB may be mentioned in particular as representatives of this category of cationic lipids. Other compounds, such as DOSC and ChOSC, are characterized by the presence of a choline group in place of the quaternary ammonium group. Another category of cationic lipids, lipopolyamines, has also been described. In compounds of this type, the cationic group is represented by the L-5-carboxyspermine radical which contains four ammonium groups, two primary and two secondary. DOGS and DPPES are particularly among these lipopolyamines. These lipopolyamines are most particularly effective- for transfecting primary endocrine cells.

Advantageously, the lipofectants suited to the invention may also be chosen from lipopolyamines whose polyamine region corresponds to the general formula (II)

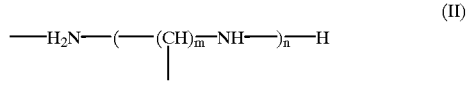

(II)

in which m is an integer greater than or equal to 1 and n is an integer greater than or equal to 1, it being possible for m to vary for the different carbon groups between two amines. Preferably, m is between 2 and 6 inclusive and n is between 1 and 5 inclusive. Even more preferably, the polyamine region is represented by spermine, thermine or one of the analogues thereof which has conserved the properties of binding to the DNA. As regards the lipophilic region, it is represented by at least one saturated or unsaturated hydrocarbon chain, cholesterol, a natural lipid or a synthetic lipid capable of forming lamellar or hexagonal phases, linked covalently to the hydrophilic region.

Patent application EP 394,111 describes other lipopolyamines of general formula III which may be used within the context of the present invention:

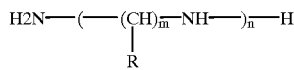

in which R represents in particular a radical of general formula $(R_1R_2)N-CO-CH-NH-CO-$.

Representative examples of these lipopolyamines which may be mentioned more particularly are dioctadecylamidoglycylspermine (DOGS) and palmitoylphosphatidylethanolamine 5-carboxyspermylamide (DPPES).

The lipopolyamines described in patent application FR 94/14596 may also be used advantageously as transfection agent according to the invention. They are represented by the general formula IV above in which R represents

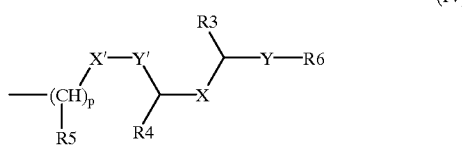

with

X and X' representing, independently of each other, an oxygen atom, a methylene group $-(CH_2)_q-$ with q equal to 0, 1, 2 or 3, or an amino group $-NH-$ or $-NR'-$ with R' representing a $C_1$ to $C_4$ alkyl group, Y and Y' representing, independently of each other, a methylene group, a carbonyl group or a C=S group, $R_3$, $R_4$ and $R_5$ representing, independently of each other, a hydrogen atom or a substituted or unsubstituted $C_1$ to $C_4$ alkyl radical, with it being possible for p to range between 0 and 5, $R_6$ representing a cholesterol derivative or an alkylamino group $-NR_1R_2$ with $R_1$ and $R_2$ representing, independently of each other, a saturated or unsaturated linear or branched $C_{12}$ to $C_{22}$ aliphatic radical.

Representative examples of these lipopolyamines which may be mentioned most particularly are 2,5-bis(3-aminopropylamino)pentyl (dioctadecylcarbamoylmethoxy) acetate and 1,3-bis(3-aminopropylamino)-2-propyl (dioctadecylcarbamoylmethoxy)acetate, hereinafter referred to as lipopolyamine A.

Patent applications EP 394,111 and FR 94 145 96 also describe a process which may be used for the preparation of the corresponding lipopolyamines.

Lastly, more recently, novel lipopolyamines, which can also be upgraded within the context of the present invention, have been described in patent application FR 95/134 90. Representatives of these lipopolyamines which may be mentioned more particularly are the following:

lipopolyamine B:

lipopolyamine C:
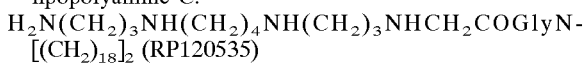

lipopolyamine D:

Within the context of the invention, dioctadecylamidoglycylspormine (DOGS), palmditoylphosphatidylethanolamine 5-carboxyspermylamide (DPPES), 2,5-bis(3-aminopropylamino)pentyl (dioctadecylcarbamoylmethoxy) acetate, 1,3-bis(3-aminopropylamino)-2-propyl (dioctadecylcarbamoylmethoxy)acetate,
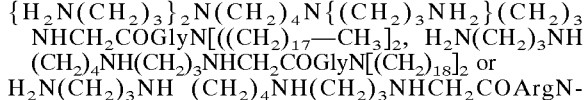
may be used particularly advantageously.

In order to obtain an optimum effect for the compositions of the invention, the respective proportions of the polyamine and the nucleic acid are preferably determined such that the ratio R of positive charges on the transfection agent/negative charges on the nucleic acid is between 0.1 and 10 and more preferably between 0.5 and 6.

The presence of a compound according to the invention within a transfecting composition makes it advantageously possible to decrease the amount of transfection agent considerably. This results in a markedly reduced toxicity which consequently makes possible, for example, the transfection of cells which are sensitive at the source to the transfection agent such as, for example, haematopoietic cells with the lipopolyamines. Lastly, as the examples below demonstrate, the transfecting power of the compositions according to the invention is greater than that obtained with the standard transfecting compositions.

In the compositions of the present invention, the nucleic acid may either be a deoxyribonucleic acid or a ribonucleic acid. It may be sequences of natural or artificial origin, and in particular genomic DNA, cDNA, mRNA, tRNA, rRNA, hybrid sequences or synthetic or semi-synthetic sequences. These nucleic acids may be of human, animal, plant, bacterial, viral, etc. origin. They may be obtained by any technique known to those skilled in the art, and in particular by the screening of banks, by chemical synthesis or by mixed methods including the chemical or enzymatic modification of sequences obtained by the screening of banks. They may moreover be incorporated into vectors, such as plasmid vectors.

As regards more particularly the deoxyribonucleic acids they may be single- or double-stranded. These deoxyribonucleic acids may code for therapeutic genes, sequences for regulating transcription or replication, antisense sequences, regions for binding to other cell components, etc.

In the sense of the invention, the term therapeutic gene is understood in particular to refer to any gene which codes for a protein product having a therapeutic effect. The protein product thus encoded may be a protein, a peptide, etc. This protein product may be homologous with respect to the target cell (that is to say a product which is normally expressed in the target cell when the latter exhibits no pathology). In this case, the expression of a protein makes it possible, for example, to overcome an insufficient expression in the cell or the expression of a protein which is inactive or weakly active on account of a modification, or alternatively of overexpressing the said protein. The therapeutic gene may thus code for a mutant of a cell protein, having increased stability, modified activity, etc. The protein product may also be heterologous with respect to the target cell. In this case, an expressed protein may, for example, make up or provide an activity which is deficient in the cell, enabling it to combat a pathology or to stimulate an immune response.

In the sense of the present invention, among the therapeutic products which may more particularly be mentioned are enzymes, blood derivatives, hormones, lymphokines, interleukins, interferons, TNF, etc. (FPR 9203120), growth factors, neurotransmitters or their precursors or synthetic enzymes, trophic factors: BDNF, CNTF, NGF., IGF, GMF, aFGF, bFGP, VEGF, NT3, NT5, HARP/pleiotrophin, genes corresponding to the proteins involved in the metabolism of lipids, of apolipoprotein type chosen from apolipoproteins A-I, A-II, A-IV, B, C-I, C-II, C-III, D, E, F, G. H, J and apo (a), metabolic enzymes such as, for example, lipoprotein lipase, hepatic lipase, lecithin cholesterol acyltransferase, 7-alpha-cholesterol hydroxylase, phosphatidic acid phosphatase, or lipid transfer proteins such as cholesterol ester transfer protein and phospholipid transfer protein, a protein for binding HDLs or a receptor chosen, for example, from LDL receptors, chylomicron-remnant receptors and scavenger receptors, dystrophin or minidystrophin (FR 9111947), GAX protein, CFTR protein associated with mucoviacidosis, tumour-suppressant genes: p53, Rb, Rap1A, DCC, k-rev, etc. (FR 9304745), genes coding for factors involved in coagulation: factors VII, VIII, IX, genes involved in DNA repair, suicide genes (thymidine kinase, cytosine deaminase), etc.

The therapeutic gene may also be an antisense sequence or a gene whose expression in the target cell makes it possible to control the expression of genes or the transcription of cellular NA. Such sequences may, for example, be transcribed in the target cell into complementary RNA of cellular mRNA and thus block their translation into protein, according to the technique described in patent EP 140,308. The antisense sequences also comprise the sequences coding for ribozymes which are capable of selectively destroying target RNA (EP 321,201).

As indicated above, the nucleic acid may also contain one or more genes coding for an antigenic peptide, capable of generating an immune response in humans or animals. In this particular embodiment, the invention thus makes it possible to produce either vaccines or immunotherapeutic treatments applied to humans or to animals, in particular against microorganisms, viruses or cancers. They may in particular be antigenic peptides specific for Epstein Barr virus, for HIV virus, for hepatitis B virus (EP 185,573), for pseudo-rabies virus or alternatively specific for tumours (EP 259,212).

Preferably, the nucleic acid also comprises sequences which allow the expression of the therapeutic gene and/or of the gene coding for the antigenic peptide in the desired cell or organ. These may be sequences which are naturally responsible for expression of the gene considered when these sequences are capable of functioning in the infected cell. They may also be sequences of different origin (responsible for the expression of other proteins, or even synthetic). In particular, they may be promoter sequences for eukaryotic or viral genes. For example, they may be promoter sequences derived from the genome of the cell which it is desired to infect. Similarly, they may be promoter sequences derived from the genome of a virus. In this regard, there may for example be mentioned the promoters of genes E1A, MLP, CKV, RSV, etc. In addition, these expression sequences may be modified by addition of activation sequences, regulation sequences, etc.

Moreover, the nucleic acid may also contain, in particular upstream of the therapeutic gene, a signal sequence which directs the therapeutic product synthesized into the secretion pathways of the target cell. This signal sequence may be the natural signal sequence of the therapeutic product, but it may also be any other functional signal sequence, or an artificial signal sequence.

More preferably, the compositions of the invention also comprise one or more neutral lipids. Such compositions are particularly advantageous, especially when the ratio R is low. The Applicant has indeed shown that the addition of a neutral lipid makes it possible to improve the formation of the nucleolipid particles and, surprisingly, to promote the penetration of the particle into the cell by destabilizing its membrane.

More preferably, the neutral lipids used in the context of the present invention are lipids containing 2 fatty chains.

In a particularly advantageous manner, natural or synthetic lipids, which may be zwitterionic or devoid of ionic charge under the physiological conditions, are used. They may be chosen more particularly from dioleoylphosphatidylethanolamine (DOPE), oleoylpalmitoylphosphatidylethanolamine (POPE), di-atearoyl, -palmitoyl or myristoyl phosphatidylethanolamine as well as derivatives thereof N-methylated 1 to 3 times, phosphatidylglycerols, diacylglycerols, glycosyldiacylglycerols, cerebrosides (such as galactocerebrosides in particular), sphingolipids (such as sphingomyelins in particular) or alternatively asialogangliosides (such as asialoGM1 and GM2 in particular).

These various lipids may be obtained either by synthesis or by extraction from organs (example: brain) or from eggs, by standard techniques well known to those skilled in the art. In particular, the extraction of natural lipids may be performed using organic solvents (see also Lehninger, Biochemistry).

The compositions of the invention, using a lipofectant as transfection agent, preferably comprise from 0.1 to 20 equivalents of neutral lipid per one equivalent of lipopolyamine and, more preferably, from 1 to 5. In the case in which the transfection agent is a cationic polymer, the compositions of the invention comprise, in addition to the cationic polymer in the ratios mentioned above, from 0.1 to 20 molar equivalents of neutral lipid per 1 molar equivalent of nucleic acid phosphate, and more preferably from 1 to 5.

The compositions according to the invention may be formulated for the purpose of topical, cutaneous, oral, rectal, vaginal, parenteral, intranasal, intravenous, intramuscular, subcutaneous, intraocular, transdermal, etc. administration. The pharmaceutical compositions of the invention preferably contain a vehicle which is pharmaceutically acceptable for an injectable formulation, in particular for direct injection into the desired organ, or for topical administration (to skin and/or mucous membrane). They may in particular be sterile, isotonic solutions or dry compositions, in particular freeze-dried compositions, which, by addition, depending on the case, of sterilized water or of physiological saline, allow injectable solutions to be made up. The doses of nucleic acid used for the injection and the number of administrations may be adapted according to various parameters, and in particular according to the mode of administration used, the pathology concerned, the gene to be expressed, or alternatively the desired duration of the treatment.

They may advantageously be used to transfect a wide variety of cell types such as, for example, haematopoietic cells, lymphocytes, hepatocytes, endothelial cells, melanoma carcinoma and sarcoma cells, smooth muscle cells, neurons and astrocytes.

The present invention thus provides a particularly advantageous method for the treatment of diseases, using the in vivo, ex vivo or in vitro transfection of a nucleic acid capable of correcting the said disease, in combination with a transfection agent of cationic polymer or lipofectant type, and a compound as defined above. More particularly, this method may be applied to diseases resulting from a deficiency of a protein or nucleic acid product and the nucleic acid administered codes for the said protein product or contains the sequence corresponding to the said nucleic acid product. The compositions according to the invention are particularly advantageous on account of their bioavailability and their high level of transfection.

The present invention also relates to any use of a compound consisting, partly or totally, of peptide units (LysThrProLysLysAlaLysLysPro) (SEQ ID No.: 1) and/or (AlaThrProAlaLysLysAlaAla) (SEQ ID No.: 2) with it being possible for the number of these units to range between 2 and 10, in order, when they are coupled to a cell receptor ligand, an antibody or an antibody derivative, to target a nucleic acid towards cells which express the corresponding receptors or antigens. In this perspective, a potential ligand, antibody or antibody derivative is coupled to the said compound and the transfection power of this chimeric molecule is assessed relative to the compound alone.

The present invention also covers any use of an oligopeptide selected from:
(AlaThrProAlaLysLysAlaAlaAlaThrProAlaLysLysAlaAla) (COOH) (SEQ ID No.: 3), (LysThrProLysLysAlaLysLysProLysThrProLysLysAlaLysLysPro) (COOH) (SEQ ID No.: 4), AlaThrProLysLysSerAlaLysLysThrProLysLysAlaLysLysPro (COOH) (SEQ ID No.: 5), LysLysAlaLysSerProLysLysAlaLysAlaAlaLysProLysLysAlaProLysSerProAlaLysAlaLysAla (COOH) (SEQ ID No.: 6), SerArgSerArgTyrTyrArgGlnArgGlnArgSer-ArgArgArgArgArgArg (COOH) (SEQ ID No.: 7) and ArgArgArgLeuHisArgIleHisArgArgGlnHisArgSerCysArgArgArgLysArgArg (COOH) (SEQ ID No. 8)
in order to carry out the in vitro, ex vivo and/or in vivo transfer of at least one nucleic acid, the said oligonucleotide being or not being associated with a targeting element.

The present invention will be described more fully using the examples which follow, which should be considered as being non-limiting illustrations.

Equipment and methods:

Plasmids used for the in vivo transfer of genes

The constructions used to demonstrate the activity of the compositions of the invention are plasmids containing the gene coding for luciferase (Luc).

These plasmids are, in particular, pCXV luc, pXL 2621 and pXL 2622, which all contain the gene coding for luciferase (taken from the vector pGL2, Promega) downstream of the cytomegalovirus (CMV) promoter extracted from pCDNA3 (Invitrogen). pCMV luc and pXL 2622 are derived from a pGL2 vector, pXL 2621 from a control pGL2 vector, and, in all these vectors, the SV40 promoter has been replaced by the CMV promoter.

In general, the plasmids are obtained by the technique of precipitation with PEG (Ausubel) and stored in 10 mM tris 1 mM EDTA pH 8 at 4° C. at a concentration of about 10 $\mu$g of DNA per $\mu$l.

H: LysThrProLysLysAlaLysLysProLysThrProLysLysAlaLysLysPro (COOH) (SEQ ID No.: 4) 18AA.

N: AlaThrProAlaLysLysAlaAlaAlaThrProAlaLysLysAlaAla (COOH) (SEQ ID No.: 3) 16AA nls-H: ProLysLysLysArgLysValβAlaLysThrProLysLysAlaLysLysProLysThrProLysLysAlaLysLysPro (COOH) (SEQ ID No.: 9) 26AA;

PR1:
ArgArgArgLeuHisArgIleHisArgArgGlnHisArgSerCysArgArgArgLysArgArg (SEQ ID No.: 8) 21AA

PR2:
SerArgSerArgTyrTyrArgGlnArgGlnArgSerArgArg-ArgArgArgArg (SEQ ID No.: 7)

They were prepared as follows:

2.1 N: AlaThrProAlaLysLysAlaAlaAlaThrProAlaLysLysAlaAla (COOH) (SEQ ID No.: 3)

This oligopeptide was synthesized in the form of the trifluoroacetic acid salt using an Applied Biosystem 431A peptide synthesizer, on an HMP resin (Applied Biosystem) and according to an FMOC strategy. After the synthesis, the peptide was released from the resin by treatment for 90 minutes in the presence of 1/19 water/TFA solution. After filtration, the solution is concentrated on a rotary evaporator and the peptide is then precipitated twice, by addition of tert-butyl methyl ether, from a solution in TFA. The final pellet is washed with tert-butyl methyl ether and then dried. The peptide is dissolved in 5 ml of water, filtered and purified by reverse-phase HPLC on a C18 100 A column (Biorad RSL). The peptide is purified by with the aid of a gradient of 0 to 25% of acetonitrile, 0.07% TFA in water 0.07% TFA. The purity of the peptide obtained is greater than 95% and its solubility in water is 100 mg/ml.

2.2 nls: ProLysLysLysArgLysVal (SEQ ID. NO: 9, residues 1–7)

This oligopeptide was synthesized in the form of the trifluoroacetic acid salt according to the procedure described above, using 2/40/3/1/2 (v/v) water/TFA/phenol/ethanedithiol/thioanisole solution for the cleavage. The purity of the peptide obtained is greater than 95% and its solubility in water is 100 mg/ml at pH 2.1.

2.3 H: LysThrProLysLysAlaLysLysProLysThrProLysLysAlaLysLysPro (COOH) (SEQ ID No.: 4) and nls-H: ProLysLysLysArgLysVal-β-AlaLysThrProLysLysAlaLysLysProLysThrProLysLysAlaLysLysPro (COOH) (SEQ ID No.:9)

These oligopeptides are synthesized in the form of the trifluoroacetic acid salts according to the procedure described above. To do this, the resin is divided into two batches. A first batch intended for the synthesis of H is treated for the cleavage with 40/3/1/2/2 (v/v) TFA/phenol/ethanedithiol/thioanisole/water solution. The purity of the peptide obtained is greater than 90% and its solubility in water is 10 mg/ml at pH 2.1. The synthesis is continued on the second batch of resin so as to obtain nls-β-Ala-H. The cleavage solution used is identical to the previous one. The purity of the peptide obtained is greater than 95% and its solubility in water is 10 mg/ml at pH 2.1.

2.4 PR1: ArgArgArgLeuHisArgtIleHisArgArgIle-HisArgSerCysArgArgArgLysArgArg (SEQ ID No.: 8) and PR2: SerArgSerArgTyrTyrArgGlnArglnArgaer-ArgArgArgArgArgArg (SEQ ID No.: 7)

These oligopeptides are assembled in several steps, in a solid phase synthesis according to the BocBenzyl technique. The starting resin is a Boc-L-Arg(Tos)Pam resin (0.48 meq/g). The deprotection and coupling process used is as follows:

| | |
|---|---|
| 1- 55% TFA in dichloromethane (DCM) | 1 × 2 mn |
| 2- 55% TFA in dichloromethane | 1 × 30 mn |
| 3- DCM | 2 × 1 mn |
| 4- DMF | 3 × 1 mn |
| 5- Coupling | |
| 6- DMF | 2 × 1 mn |
| 7- DCM | 2 × 1 mn |

For each step, 10 ml of solvent are used per gram of peptide resin used. The coupling of all the amino acids (in three-fold excess) is carried out in DMF in the presence of BOP, Hobt and DIEA. Each coupling step is controlled by the ninhydrin test.

The final peptide is recovered from the resin and deprotected fully with liquid hydrofluoric acid. 10 ml of HF are used per gram of resin peptide at 0° C. for 45 minutes in the presence of para-cresol and ethanedithiol. After evaporation of the hydrofluoric acid, the crude reaction mixture is washed with ether, dissolved in trifluoroacetic acid, precipitated with ether and dried.

3. Lilofectant agents used
Lipopolyamine A:
d,1-3-bis(3-aminopropylamino)-2-propyl (dioctadecylcarbamoylmethoxy)acetate (RP115335)
Lipopolyamine B:
$\{H_2N(CH_2)_3\}_2N(CH_2)_4N\{(C_2)_3NH_2\}(CH_2)_3NHCH_2COGlyN[(CH_2)_{17}-CH_3]_2$ (RP120525)
Lipopolyamine C:
$H_2N(CH_2)_3NH(CH_2)_4NH(CH_2)_3NHCH_2COGlyN-[(CH_2)_{18}]_2$(RP120535)
Lipopolyamine D:
$H_2N(CH_2)_3NH(CH_2)_4NH(CH_2)_3NHCH_2COArgN-[(CH_2)_{18}]_2$ (RP120531)

EXAMPLE 1 in vitro transfer of nucleic acid into NIH 3T3 cells

This example describes the in vitro transfer of nucleic acids (on cell cultures) using a composition according to the invention comprising the nucleic acid, a compound according to the invention and a lipopolyamine, under various pH and buffer conditions.

1. A mixture of 10 μl composed of the following is prepared:
   0.5 μg of pCKV-luc plasmid DNA, 0.25 μg of a compound according to the invention, in a buffer solution as identified,
   40 mM dioctadecylamidoglycylspermine (DOGS) in charge ratios X as indicated in each of the tests.

2. $5 \cdot 10^4$ cells from the NIH3T3 lines are incubated with the above mixture at 37° C., under an atmosphere of 5% $CO_2$ for 4 hours. The cells are then washed and recultured for 48 hours in a medium containing 10% serum (DMEM 10% SVF).

The cell carpet is then lysed in 50 μl of lysis buffer (Promega), recovered and then centrifuged at 20,000 g for 5 minutes.

The luciferase activity is measured on 4 μl of supernatant by adding 20 μl of substrate (Promega). The reading is taken on a LKB luminometer, cumulating the RLUs (relative light units) over 20 seconds.

The results are given in Tables 1 and 2 below.

3. Compaction in 150 mM NaCl, 10 MM HEPES* (* N-(2-hydroxyethyl)piperazine-N'-(2-ethanesulphonic acid) at pH 7.1

TABLE 1

| DOGS/DNA charge ratio | Without compound (R.L.U) | With H (R.L.U) |
|---|---|---|
| 0.8× | 32 | 850 |
| 1.8× | 220 | 23700 |
| 3× | 5400 | 21750 |

4. Compaction in 5% D-glucose. 150 mM NaCl, with 10 mM HEPES (pH of the compaction solution: 7.2)

TABLE 2

| DOGS/DNA charge ratio | Without compound (R.L.U) | With H (R.L.U) | With N (R.L.U) |
|---|---|---|---|
| 0.8× | 880 | 44000 | 1450 |
| 1.8× | 6600 | 156500 | — |
| 3× | 22000 | 297500 | 90300 |

Better results are observed in all of the tests when the compacting composition combines a compound according to the invention with DOGS. It turns out to be possible to decrease substantially the amount of DOGS without having a prejudicial effect on the transfection capacity of the corresponding composition.

EXAMPLE 2

Transfection test in the presence of a neutral livid
A mixture of 10 μl composed of the following is prepared:
   0.5 μg of pCMV-luc plasmid DNA, 0.25 μg of a compound according to the invention, in 150 mM NaCl buffer and 10 μM phosphate buffer solution, pH 7.4,
   40 mM of dioctadecylamidoglycylspermine (DOGS) in charge ration X as indicated in each of the tests, in the presence of dioleoylphosphatidylethanolamine (DOPE) with DOGS/DOPE equal to ½.

In this particular case, a 40 mM ethanolic DOGS solution is mixed with an equal volume of an 80 mM dioleoylphosphatidylethanolamine (DOPE) solution, prepared in a chloroform/ethanol (⅕) mixture. Thus, for one equivalent of DOGS the composition contains two equivalents of DOPE.

$10^5$ cells from NIH3T3 lines are incubated with this mixture under the conditions described in the above example. After incubation, these cells are treated according to the procedure of the same example. The results are given in the table below.

TABLE 3

| DOGS/DNA charge ratio | Without compound (RLU) | With H (RLU) | With nls-H chimera (RLU) |
|---|---|---|---|
| 0.8 × D/D | 24 | 3175 | 760 |
| 1 × D/D | 19 | 7410 | 2380 |
| 1.8 × D/D | 1800 | 39500 | 52800 |

These results confirm those observed in Example 1. In the presence of a basic compound according to the invention, and more particularly H, it is possible to reduce the amount of lipofectant by half.

EXAMPLE 3

Variation of the compound according to the invention/DNA ratio within a transfecting composition according to the invention.

3.1: In the presence of a DOGS composition
1. A mixture of 10 μl composed of the following is prepared:
   0.75 μg of pCMV-luc plasmid DNA and a compound according to the invention in the ratio indicated, in 5% D-glucose, 150 mM NaCl buffer solution, with 10 mM HEPES (pH of the compaction solution: 7.2),
   40 mM dioctadecylamidoglycylspermine (DOGS) in a charge ratio of 1.8 X.

2. $4 \cdot 10^5$ cells from NIH3T3 lines are incubated with the above mixture at 37° C., under an atmosphere of 5% $CO_2$ for 4 hours. The cells are then washed and recultured for 48 hours in a medium containing 10% serum (DMEM 10%SVF). The cell carpet is then lysed, 45 hours after the transfection, in 100 μl of lysis buffer (Promega), recovered and then centrifuged at 20,000 g for 5 minutes. The luciferase activity is measured on 5 μl of the supernatant, adding 25 μl of substrate (Promega). The reading is taken on an LKB luminometer, cumulating the RLUs (relative light units) over 20 seconds.

The results are featured in Table 4 below.

TABLE 4

| PEP/DNA w/v | With H (RLU) | With H-nls (RLU) | With N (RLU) |
|---|---|---|---|
| 0 | 2150 | 2150 | 2150 |
| 0.25 | 3300 | 38,000 | 35,000 |
| 0.5 | 45,000 | 100,000 | 35,000 |
| 1 | 84,000 | 105,000 | 13,000 |
| 2 | 105,000 | 200,000 | 20,000 |

3.2: In the presence of 1.8X DOGS/DOPE

The process is performed as in the procedure described above in 3.1, but using as transfecting agent a 40 mM solution of 1.8x dioctadecylamidoglycylspermine (DOGS) in the presence of dioleoylphosphatidyl-ethanolamine (DOPE) with DOGS/DOPE equal to ½, prepared according to the procedure presented in Example 2.

Table 5 gives the results observed.

TABLE 5

| COMPOUND/DNA w/v | H (RLU) | H-nls (RLU) | N (RLU) |
|---|---|---|---|
| 0 | 580 | 580 | 580 |
| 0.25 | 13,000 | 5600 | 7600 |
| 0.5 | 11,000 | 18,500 | 1800 |
| 1 | 14,100 | 36,000 | 13,600 |
| 2 | 16,500 | 58,000 | 14,100 |

EXAMPLE 4

Variation of the compound according to the invention/DNA ratio within a transfecting composition according to the invention, using a transfection agent other than DOGS.

3.1: In the Presence of 1.3-bis-(3-aminopropylamino)-2-propyl (dioctadecylcarbamoylmethoxy)acetate (lipopolyamine A)

1. A mixture of 10 μl composed of the following is prepared:

0.55 μg of pCMV-luc plasmid DNA and a compound according to the invention, in the ratio indicated, in 150 μm NaCl buffer solution, 1,3-bis (3-aminopropylamino)-2-propyl (dioctadecylcarbamoylmethoxy)acetate in in the charge ratios indicated.

2. 5–10$^4$ cells from NIH3T3 lines are incubated with the above mixture at 37° C., under an atmosphere of 5% $CO_2$ for 4 hours. The cells are then washed and recultured for 48 hours in a medium containing 10% serum (DMEM 10%SVF). The cell carpet is then lysed, 45 hours after the transfection, in 100 μl of lysis buffer (Promega), recovered and then centrifuged at 20,000 g for 5 minutes. The luciferase activity is measured on 10 μl of the supernatant, adding 50 μl of substrate (Promega). The reading is taken on a Berthold lumat 950® luminometer, cumulating the RLUs (relative light units) over 10 seconds. The results are featured in Table 6 below.

TABLE 6

| $NH_2$ in the lipofectant/ phosphates in the DNA ratio | LIPOFECTANT | | | | | |
|---|---|---|---|---|---|---|
| | Without compound · $10^6$ · RLU | With H · $10^6$ · RLU | | | With nls-H · $10^6$ · RLU | |
| | | Compound/DNA ratio | | | | |
| | 0 | 0.5 | 1 | 2 | 0.5 | 1 | 2 |
| 1.8x | 3.9 | 30.4 | 32.7 | 4.1 | 52.4 | 58.5 | 39.3 |
| 3x | 8.9 | 41.5 | 61.3 | 16.6 | 64.1 | 60.4 | 49.2 |
| 6x | 6.2 | 23.6 | 22.3 | 15.6 | | | |

4.2: In the presence of PEI 800K

1. The process is performed according to the procedure described in 4.1 and in an identical medium, using PEI800K as lipofectant. The results are featured in Table 7 below.

TABLE 7

| Equivalent of amines in the polymer to phosphate in the DNA | PEI 800K | | | | | |
|---|---|---|---|---|---|---|
| | Without compound · $10^6$ · RLU | H · $10^6$ · RLU | | | nls-H · $10^6$ · RLU | |
| | | Compound/DNA ratio | | | | |
| | 0 | 0.5 | 1 | 2 | 0.5 | 1 | 2 |
| 6 | 7.7 | 4.9 | 7 | 12.3 | 4 | 7.3 | 8.8 |
| 9 | 5 | 8 | 11.6 | 4 | 16.3 | 11 | 12.1 |
| 12 | 7.5 | 11.3 | 17.1 | 1.2 | | | |

EXAMPLE 5

In vivo transfer into muscle cells

The corresponding tests are performed using the following procedures and materials:

Model: The injection is made into the cranial tibial muscle of adult C57 b16 or OP1 mice (more than 8 weeks old)

Procedure: The DNA is diluted to 0.5 mg/ml in a solution which will have final concentrations of 150 nM NaCl and 5% D-glucose. In certain groups, before injection, peptide as a 1 mg/ml solution in water is added to the DNA in an amount which is sufficient to reach the weight/weight ratios indicated. Incubation for at least 20 minutes at room temperature is carried out before the injection is made. Determination of the results: Two days after the injection, the muscle is removed and chopped up in 750 μl of lysis buffer (Promega E153A) supplemented with aprotinin (Sigma).

The sample is homogenized in a grinder (Heidolf) and 10 μl are used to measure the luciferase activity. This measurement is taken with a Lumat 9501 luminometer (Berthold), by totalizing the emission produced for 10 seconds after addition of 50 μl of luciferase substrate (Promega) to 10 μl of the sample. The background noise measured before addition of substrate is subtracted from this total, and the activity is expressed as total RLU (relative light units) (relative to 750 ml of lysis buffer).

To do this, 40 μl (20 μg of DNA) are injected, in the presence of HEPES at pH 7.4 final concentration of 5 mM in the solution, followed by addition of the lipopolyamine C(RPR 120 535) in a ratio 0.01 nmol/μl of DNA 20 minutes before injection:

TABLE 8

| Peptide, peptide/DNA weight/weight ratio | Average RLU | RLU standard deviation | number of animals |
|---|---|---|---|
| without peptide | 15 228 125 | 14 618 681 | 6 |
| nls-H, 0.025 weight/weight + lipopolyamine C | 42 722 500 | 66 485 348 | 6 |

These results confirm the beneficial effect of the combination of a lipopolyamine with a compacting agent according to the invention on the in vivo transfection of a nucleic acid into muscle.

EXAMPLE 6

In vivo transfer of compositions claimed into tumour cells

The corresponding tests are carried out on adult (>9 weeks) female C57/BL mice carrying tumours of type 3LL (Lewis Lung carcinoma) obtained by passing fragments of tumour from animal to animal, implanted under the skin of the flank.

As regards the solutions injected, they are prepared as follows: the DNA is first dissolved in the buffer, the peptide is then optionally added and, after 20 minutes, a solution of cationic lipids at high concentration (20 or 40 mM) is added to the mixture. After addition of all these products, the mixture contains, besides the DNA, the peptide and the cationic lipid, 150 mM NaCl, 5% D-glucose and 5 mM MES pH 6.2. In the case of the last two series with lipopolyamine C (RPR 120 535), the injection vehicle is 75 mM NaCl and 150 =M NaCl, 5% D-glucose respectively. The injection is made 20 to 30 minutes after the solution has been prepared.

Each transfecting composition (see Tables 9 and 10 for their respective specificities) is injected into the tumour 7 days after implantation, the mouse being anaesthetized with a ketamine 130 mg/kg+xylazine (4 mg/kg) mixture.

Two days after the injection, the tumour tissue is removed, weighed and then chopped up and ground in 500 $\mu$l of lysis buffer (Promega cell lysis buffer E153 A). After centrifugation (20,000 g for 10 minutes), 10 $\mu$l are taken and used to evaluate the luciferase activity by measuring the total light emission obtained after mixing with SO ;l of reagent (Promega luciferase assay substrate) in a Lumat LB 9501 luminometer (Berthold), with integration over 10 seconds.

The resulting activity is expressed as RLUs (relative light units) estimated in the entire tumour lysis supernatant, or as RLU per $\mu$g of DNA injected.

Table 9 gives the results obtained in the presence of various lipopolyamines A, B, C or D and Table 10 in the presence of PEI.

TABLE 9

| Plasmid | | Peptide | | Cationic lipid | | Result, RLU/tumour | | Number of |
|---|---|---|---|---|---|---|---|---|
| $\mu$g/ tumour | [DNA] $\mu$g/$\mu$l | reference | pept/DNA w/w | reference | nmol/ $\mu$g DNA | average | standard deviation | animals treated |
| 20 | 2 | | | | | 0 | 0 | 5 |
| 20 | 2 | | | A | 1.8 | 142 300 | 121 418 | 5 |
| 20 | 2 | H | 1 | ◄ | 1.8 | 301 730 | 243 166 | 5 |
| 30 | 2 | | | ◄ | 3 | 99 775 | 128 726 | 6 |
| 30 | 2 | H | 1 | ◄ | 3 | 1 340 460 | 1 771 624 | 5 |
| 7.5 | 0.5 | | | A | 3 | 88 712 | 49 314 | 5 |
| 7.5 | 0.5 | H | 1 | ◄ | 3 | 383 313 | 234 713 | 6 |
| 7.5 | 0.5 | H | 1.5 | ◄ | 3 | 618 025 | 530 774 | 6 |
| 15 | 1 | H | 1 | ◄ | 3 | 1 017 372 | 966 141 | 5 |
| 10 | 0.5 | H | 1.5 | C | 3 | 679 258 | 414 286 | 9 |
| 10 | 0.5 | H | 1.5 | D | 3 | 395 433 | 219 333 | 10 |
| 18.75 | 0.25 | | | C | 2 | 222 700 | 126 036 | 6 |
| 18.75 | 0.25 | Pr 2 | 0.5 | " | 2 | 1 046 050 | 612 401 | 6 |
| 20 | 0.5 | | | C | 4 | 806 467 | 887 206 | 6 |
| 20 | 0.5 | H | 1 | C | 4 | 1 348 233 | 1 674 106 | 6 |

TABLE 10

| Plasmid | | Peptide | | Poly- ethyleneimine | | Result, RLU/tumour | | Number of |
|---|---|---|---|---|---|---|---|---|
| amount injected | [DNA] $\mu$g/$\mu$l | reference | peptide/ DNA w/w | size | Eq | average | standard deviation | animals treated |
| 20 | 2 | | | | | 0 | 0 | 5 |
| 20 | 2 | | | 800K | 9 | 54 350 | 52 989 | 5 |
| 50 | 2 | | | 800K | 9 | 7 783 | 16 803 | 6 |
| 50 | 2 | H1 | 1 | 800K | 9 | 62 230 | 71 462 | 5 |
| 50 | 2 | | | 800K | 12 | 6 733 | 16 493 | 6 |
| 50 | 2 | H1 | 1 | 800K | 12 | 72 700 | 150 300 | 5 |

TABLE 10-continued

| Plasmid amount injected | [DNA] μg/μl | Peptide reference | peptide/ DNA w/w | Poly- ethyleneimine size | Eq | Result, RLU/tumour average | standard deviation | Number of animals treated |
|---|---|---|---|---|---|---|---|---|
| 40 | 2 | | | 800K | 18 | 470 | 1 051 | 5 |
| 40 | 2 | H1 | 1 | 800K | 18 | 82 608 | 104 443 | 6 |
| 40 | 2 | | | 800K | 24 | 1 630 | 3 645 | 5 |
| 40 | 2 | H1 | 1 | 800K | 24 | 45 750 | 63 942 | 5 |
| 10 | 0.5 | H1 | 1.5 | 50K lactose | 12 | 14 152 | 16 946 | 11 |
| 10 | 0.5 | H1 | 1.5 | 50K maltose | 12 | 12 942 | 22 853 | 11 |

EXAMPLE 7

In vitro transfer of nucleic acid into 3LL cells

This example describes the in vitro transfer of nucleic acids (on cell cultures) using a composition according to the invention comprising the nucleic acid, a compound according to the invention chosen from protamine derivatives and a lipopolyamine in a solution of 75 mM NaCl final.

A mixture of 10 μl composed of the following is prepared: 0.5 μg of pCMV-luc plasmid DNA, 0.5 μg of PR1 or PR2 a compound according to the invention, in a solution of 75 mM NaCl final lipopolyamine C (RPR 120535) in charge ratios as indicated in each of the tests listed in Table 11 below.

$1 \times 10^5$ $^3$LL cells (in 250 μl of DMEM culture medium with 10% foetal calf serum) are incubated with the above mixture at 37° C. under a 5% $CO_2$ atmosphere for 4 hours. 500 μl of culture medium are added and the cells are recultured. The following day, the cells are washed and recultured for 24 hours in the same medium containing 10% foetal calf serum.

The cell carpet is then lysed in 100 μl of lysis buffer (Promega). The luciferase activity is measured by adding 50 μl of substrate (Promega). The reading is taken on an LB luminometer by cumulating the RLUs (relative light units) over 10 seconds.

Tables 11 and 12 give the tests with PR1 and PR2 respectively.

TABLE 11

| Lipopolyamine C/DNA CHARGE RATIO | WITHOUT COMPOUND (RLU) | WITH PR2 (RLU) |
|---|---|---|
| 4× | 107 289 | 447 214 |
| 6× | 77 396 | 1 182 641 |
| 8× | 14 512 | 729 285 |

TABLE 12

| Lipopolyamine C/DNA CHARGE RATIO | WITHOUT COMPOUND (RLU) | WITH PR2 (RLU) |
|---|---|---|
| 4× | 12 037 | 6 304 |
| 6× | 901 | 113 113 |
| 8× | 328 | 294 743 |

EXAMPLE 8

In vivo injections of compacting peptides according to the invention, without lipofectant, into tumours Model:
mice of adult female nude/Swiss type
experimental tumours induced after injection of $10^7$3T3 HER2 cells subcutaneously into the flank.
injection of the transfection mixture 7 to 12 days after injecting the calls. The 'solution of DNA which is or is not compacted with peptide is injected directly into the tumour with a Hamilton-type syringe.
two days after the injection, the tumour tissue is removed, weighed and then chopped up and homogenized in 750 μl of lysis buffer (Promega cell lysis buffer E153 A). After centrifugation (20,000 g for 10 minutes), 10 μl are removed and are used to evaluate the luciferase activity by measuring the total light emission obtained after mixing with 50 μl of reagent (Promega luciferase assay substrate) in a Lumat LB 9501 luminometer (Berthold) with integration over 10 seconds.

The resulting activity is expressed as RLUs (relative light units) estimated in the entire tumour lysis supernatant.
Procedure: The DNA is diluted to 0.5 mg/ml in a solution which will contain a final concentration of the salts, the buffer and the glucose in a final amount as stated in the table of results. In certain groups, before injection, peptide dissolved to 1 mg/ml in water is added to the DNA in an amount which is sufficient to reach the weight/weight ratios indicated. Incubation for at least 20 minutes at room temperature is carried out. The mice receive an injection of 20 μl, i.e. 10 μg of DNA in total per tumour.

TABLE 13

| Buffer NaCl/ glucose/ MES or HEPES 5 mM | Peptide reference | peptide/ DNA w/w | Result, RLU/tumour average | standard deviation | Number of animals treated |
|---|---|---|---|---|---|
| 150/HEPES | | | 1 699 938 | 1 398 072 | 6 |
| | nls-H | 0.02 | 6 819 100 | 5 860 709 | 6 |
| 150/5/HEPES | | | 369 563 | 577 901 | 6* |
| | nls-H1 | 0.1 | 1 654 313 | 2 145 147 | 6* |
| | nls-H1 | 0.02 | 4 031 000 | 1 007 996 | 6* |
| | | | 931 275 | 214 229 | 4 |
| | H | 0.1 | 3 420 432 | 1 285 704 | 6 |

*mice put to sleep during the injection, by narco-neuroleptanalgesia with an Imalgene + Rompun mixture (130 mg/kg ketamine, 4 mg/kg xylazine, intraperitoneal route).

These results show that, in tumours which can be transfected by naked DNA, the addition of peptide with low peptide/DNA ratios, without combined cationic lipids, makes it possible to increase the expression of the exogenic gene when compared with the naked DNA alone.

What is claimed is:

1. A composition which is useful for the transfection of an antisense nucleic acid, comprising a transfection agent, an antisense nucleic acid, and a compound involved in the condensation of the nucleic acid, wherein the compound comprises peptide units as set forth in SEQ ID No. 1, and/or SEQ ID No. 2 repeated continuously or non-continuously, wherein the number of peptide units is between 2 and 10, or the compound comprises an oligopeptide selected from the group consisting of the oligopeptides as set forth in SEQ ID No. 7 and SEQ ID No. 8.

2. A composition which is useful for the transfection of a therapeutic gene, comprising a transfection agent, the therapeutic gene, and a compound involved in the condensation of the therapeutic gene, wherein the compound comprises peptide units as set forth in SEQ ID NO. 1 or SEQ ID NO. 2 repeated continuously or non-continuously, wherein the number of peptide units is between 2 and 10, or the compound comprises an oligopeptide selected from the soup consisting of the oligopeptides as set forth in SEQ ID NO. 7 and SEQ ID NO. 8.

3. A composition according to claim 2, wherein the peptide units are separated from each other by connections, wherein the connections are biochemical compounds, amino acids or chemical compounds.

4. A composition according to claim 3, wherein one of the connections comprises one or more amino acids.

5. A composition according to claim 2, wherein the compound is derived from histone H1.

6. A composition according to claim 5, wherein the compound is derived from the C-terminal domain of histone H1.

7. A composition according to claim 5, wherein the compound is an oligopeptide selected from the group consisting of the oligopeptides as set forth in SEQ ID No.: 4, SEQ ID No. 5, and SEQ ID No. 6.

8. A composition according to claim 2, wherein the compound is derived from the N-terminal domain of nucleoline.

9. A composition according to claim 8, wherein the compound comprises a peptide as set forth in SEQ ID No.: 3.

10. A composition according to claim 2, wherein the compound possesses a, sheet structure.

11. A composition according to claim 2, wherein the compound is also associated with a cell receptor ligand.

12. A composition according to claim 11, wherein the compound consists partly or totally of histone H1 associated with a nuclear location signal sequence.

13. A composition according to claim 12, comprising the peptide ProLysLysLysArgLysVal-βAlaLysThrProLys-LysAlaLysLysProLysThrProLys-LysAlaLysLysPro (SEQ ID No.:9).

14. A composition according to claim 2, wherein the compound is also associated with a peptide of fusogenic type which promotes the cellular transfection of the composition.

15. A composition according to claim 2, wherein the compound is polyglycosylated, sulphonated, phosphorylated and/or grafted to complex sugars or to a lipophilic agent.

16. A composition according to claim 2, wherein the transfection agent is a cationic polymer or a lipofectant.

17. A composition according to claim 16, wherein the lipofectant is a lipid that forms liposomes, furtive liposomes, immunoliposomes or target liposomes.

18. A composition according to claim 16, wherein the cationic polymer is of general formula (I):

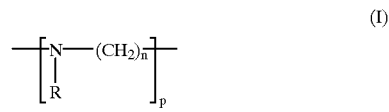

in which

R is a hydrogen atom or a group of formula

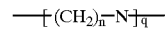

n is an integer between 2 and 10; and p and q are integers, with the sum p+q being such that the average molecular weight of the polymer is between 100 and $10^7$.

19. A composition according to claim 16, wherein the cationic polymer is selected from the group consisting of polyethyleneimine (PEI) and polypropyleneimine (PPI).

20. A composition according to claim 19, wherein the cationic polymer is selected from the group consisting of polyethyleneimine of average molecular weight 50,000 (PEI50K) and polyethyleneimine of average molecular weight 800,000 (PEI800K).

21. A composition according to claim 16, wherein the lipofectant comprises a polyamine region of general formula (II)

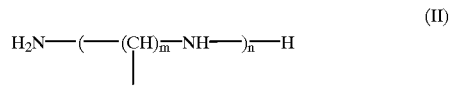

in which m is an integer greater than or equal to 2 and n is an integer greater than or equal to 1, and wherein if n is greater than 1, then m is identical or different.

22. A composition according to claim 21, wherein the polyamine region is spermine, thermine or one of the analogues thereof that binds to the therapeutic gene.

23. A composition according to claim 21, wherein the lipofectant comprises a lipophilic region represented by the general formula (IV)

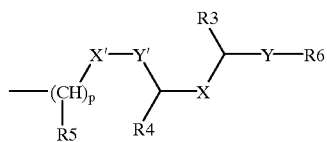

in which

X and X' represent, independently of each other, an oxygen atom, a methylene group —$(CH_2)_q$— with q equal to 0,1, 2 or 3, or an amino group —NH— or —NR'— with R' representing a C1 to C4 alkyl group, Y and Y' represent, independently of each other, a methylene group, a carbonyl group or a C=S group, $R_3$, $R_4$ and $R_5$ represent, independently of each other, a hydrogen atom or a substituted or unsubstituted $C_1$ to $C_4$ alkyl radical and p is between 0 and 5 inclusively, $R_6$ represents a cholesterol derivative or an alkylamino group —$NR_1R_2$ with $R_1$ and $R_2$ representing, independently of each other, a saturated or unsaturated linear or branched $C_{12}$ to $C_{22}$ aliphatic radical.

24. A composition according to claim 21, wherein the transfection agent comprises a lipopolyamine selected from the group consisting of dioctadecylamidoglycylspemrdne (DOGS), palmitoylphosphatidylethanolamine 5-carboxyspermylamide (DPPES), 2,5-bis(3-aminopropylamino)pentyl (dioctadecylcarbamoylmethoxy) acetate, 1,3-bis(3-aminopropylamino)2-propyl (dioctadecylcarbamoylmethoxy)acetate, $\{H_2N(CH_2)_3\}_2N(CH_2)_4N\{(CH_2)_3NH_2\}(CH_2)_3NHCH_2COGlyN[(CH_2)_{17}—CH_3]_2$, $H_2N(CH_2)_3NH(CH_2)_4NH(CH_2)_3NHCH_2COGlyN[(CH_2)_{18}]_2$ and $H_2N(CH_2)_3NH(CH_2)_4NH(CH_2)_3NHCH_2COArgN[(CH_2)_{18}]$.

25. A composition according to claim 2, wherein the transfection agent is dioctadecylamidoglycylspermine (DOGS).

26. A composition according to claim 2, wherein the therapeutic gene is encoded by a deoxyribonucleic acid.

27. A composition according to claim 2, wherein the therapeutic gene is encoded by a ribonucleic acid.

28. A composition according to claim 2 wherein the therapeutic gene is encoded by a nucleic acid that is chemically modified.

29. A composition according to claim 2, which further comprises a neutral lipid or lipids.

30. A composition according to claim 29, wherein the neutral lipid or lipids are selected from the group consisting of synthetic lipids, natural lipids, zwitterionic lipids and lipids lacking ionic charge under physiological conditions.

31. A composition according to claim 29, wherein the neutral lipid or lipids is selected from the group consisting of dioleoylphosphatidylethanolamine (DOPE), oleoylpalmitoylphosphatidylethanolamine (POPE), di-stearoyl phosphatidylethanolamine, -palmitoyl phosphatidylethanolamine, -myristoyl phosphatidylethanolamine, derivatives of di-stearoyl phosphatidylethanolamine N-methylated 1 to 3 times, derivatives of palmitoyl phosphatidylethanolamine N-methylated 1 to 3 times, derivatives of myristoyl phosphatidylethanolamine N-methylated 1 to 3 times, phosphatidylglycerol, diacylglycerol, glycosyldiacylglycerol, cerebroside, sphingolipid and asialoganglioside.

32. A method of transfer of a therapeutic gene comprising contacting a cell to be transfected with a composition according to claim 2, wherein the therapeutic gene is transferred into the cell.

33. The method of claim 32, wherein the compound is an oligopeptide selected from the group consisting of the oligopeptides as depicted in: SEQ ID No.: 3, SEQ ID No.: 4, SEQ ID No. 5, SEQ ID No. 6, SEQ ID No. 7, and SEQ ID No. 8.

34. A composition according to claim 30, wherein the neutral lipid or lipids are selected from the group consisting of galactocerebrosides, sphingomyelins, asialoGM1 and asialoGM2.

35. The method of claim 32, wherein the compound comprises peptide units as set forth in SEQ ID No.: 1 and/or SEQ ID No.: 2.

36. A method of transfer of an antisense nucleic acid comprising contacting a cell to be transfected with a composition according to claim 1, wherein the antisense nucleic acid is transferred into the cell.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 9 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:1:

Lys Thr Pro Lys Lys Ala Lys Lys Pro
1               5

(2) INFORMATION FOR SEQ ID NO:2:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:2:

Ala Thr Pro Ala Lys Lys Ala Ala
1               5

(2) INFORMATION FOR SEQ ID NO:3:

(i) SEQUENCE CHARACTERISTICS:
       (A) LENGTH: 16 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:3:

Ala Thr Pro Ala Lys Lys Ala Ala Ala Thr Pro Ala Lys Lys Ala Ala
1               5                   10                  15

(2) INFORMATION FOR SEQ ID NO:4:

(i) SEQUENCE CHARACTERISTICS:
       (A) LENGTH: 18 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:4:

Lys Thr Pro Lys Lys Ala Lys Lys Pro Lys Thr Pro Lys Lys Ala Lys
1               5                   10                  15

Lys Pro (2) INFORMATION FOR SEQ ID NO:5:

(i) SEQUENCE CHARACTERISTICS:
       (A) LENGTH: 17 amino acids
       (B) TYPE: amino acid (C) STRANDEDNESS:
        (D) TOPOLOGY: linear (ii) MOLECULE TYPE: protein (xi) SEQUENCE DESCRIPTION: SEQ ID NO:5:

Ala Thr Pro Lys Lys Ser Ala Lys Lys Thr Pro Lys Lys Ala Lys Lys
1               5                   10                  15
Pro (2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Lys Lys Ala Lys Ser Pro Lys Lys Ala Lys Ala Ala Lys Pro Lys Lys
1               5                   10                  15
Ala Pro Lys Ser Pro Ala Lys Ala Lys Ala
            20                  25

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Ser Arg Ser Arg Tyr Tyr Arg Gln Arg Gln Arg Ser Arg Arg Arg Arg
1               5                   10                  15
Arg Arg (2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Arg Arg Arg Leu His Arg Ile His Arg Arg Gln His Arg Ser Cys Arg
1               5                   10                  15
Arg Arg Lys Arg Arg
            20

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: protein -continued (xi) SEQUENCE DESCRIPTION: SEQ ID NO:9:

```
Pro Lys Lys Lys Arg Lys Val Ala Lys Thr Pro Lys Lys Ala Lys Lys
1               5                   10                  15

Pro Lys Thr Pro Lys Lys Ala Lys Lys Pro
            20                  25
```